US00PP33116P2

(12) United States Plant Patent
Deng

(10) Patent No.: US PP33,116 P2
(45) Date of Patent: Jun. 1, 2021

(54) ***LANTANA CAMARA* PLANT NAMED 'UF-1013-1'**

(50) Latin Name: ***Lantana camara* L.**
Varietal Denomination: UF-1013-1

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/974,252

(22) Filed: Dec. 2, 2020

(51) Int. Cl.
*A01H 5/02* (2018.01)
*A01H 6/86* (2018.01)

(52) U.S. Cl.
USPC ..... Plt./227
CPC ..... *A01H 6/86* (2018.05)

(58) Field of Classification Search
USPC ..... Plt./227
CPC ..... A01H 6/86; A01H 5/02
See application file for complete search history.

(56) References Cited

U.S. PATENT DOCUMENTS

PP29,292 P2 5/2018 Deng
2020/0163266 P1 5/2020 Trees

OTHER PUBLICATIONS

Cao, Z. et al., Interspecific genome size and chromosome number variation sheds new light on species classification and evolution of *Caladium* (*Araceae*), J. Am. Soc. Hort. Sci. 49:449-459 (2014).
Czarnecki II, David M. et al., Ploidy Levels and Pollen Stainability of *Lantana camara* Cultivars and Breeding Lines, HortScience 49(10):1271-1276 (2014).
Czarnecki II, David M. et al., UF-T3 and UF-T4: Two Sterile *Lantana camara* Cultivars, HortScience 47:132-137 (2012).
Deng, Zhanao et al., Infertile *Lantana camara* Cultivars UF-1011-2 and UF-1013A-2A, HortScience 52(4):652-657 (2017).
Florida Exotic Pest Plant Council (FLEPPC), Florida Exotic Pest Plant Council's 2019 List of Invasive Plant Species, available online at https://www.fleppc.org/list/list.htm.
Georgia Exotic Pest Plant Council (GA-LEPPC), List of Non-Native Invasive Plants in Georgia, available online at https://www.gaeppc.org/list/, 2020.

*Primary Examiner* — Keith O. Robinson
(74) *Attorney, Agent, or Firm* — Katherine Koenig; Koenig IP Works, PLLC

(57) ABSTRACT

A new and distinct cultivar of *Lantana camara* plant named 'UF-1013-1', characterized by its moderate vigor, mounding growth habit, dense branches, round plant form and canopy, free flowering, bright yellow and red flowers, no to little fruiting, no to few seeds, a very high level of female infertility, a very low level of pollen stainability and viability, a very high level of male infertility, lack of hybridization with *Lantana depressa*, triploidy and a unique combination of DNA marker alleles, is disclosed.

7 Drawing Sheets

ACKNOWLEDGEMENT OF FEDERAL RESEARCH SUPPORT

This invention was made with government support under FLA-GCR-005065 and FLA-GCR-005507 awarded by the National Institute of Food and Agriculture, USDA, the USDA/Tropical and Subtropical Agriculture Research (TSTAR) program, and the Florida Department of Agriculture and Consumer Service (FDACS) Specialty Crop Block Grant program. The United States government has certain rights in the invention.

Genus and species: *Lantana camara* L. (*Lantana strigocamara* R. W. Sanders).

Cultivar denomination: The present disclosure relates to *Lantana camara* cultivar 'UF-1013-1'.

BACKGROUND OF THE NEW CULTIVAR

The present invention relates to a new and distinct cultivar of *Lantana*, botanically known as *Lantana camara*, and hereinafter referred to by the name 'UF-1013-1'. *Lantana camara* (*L. camara*) is a member of the family Verbenaceae.

Plants of this species produce brightly-colored flowers, attract butterflies, tolerate harsh environmental conditions, have low maintenance requirements, and are easy to grow. Plants of *L. camara* are widely used in containers, hanging baskets, and landscapes. Commercial production of *L. camara* is widespread in the nursery industry, especially in the southern United States.

*Lantana camara* is native to Central and South Americas including the West Indies and was introduced to the United States in the 1800s. Since then, *L. camara* has escaped cultivation and become naturalized in thirteen U.S. states. In Florida, escaped *L. camara* has hybridized with *Lantana depressa*, a small and endangered Florida native species. *Lantana camara* has been listed as a Category I invasive species in Florida by the Florida Exotic Pest Plant Council (FLEPPC) (FLEPPC Invasive Plant Lists, 2019). The Georgia Exotic Pest Plant Council (GA-EPPC) has listed *L. camara* as a Category 3 exotic plant, a minor problem in the Georgia's natural areas or not yet known to be a problem in Georgia but known to be problem in adjacent states (GA-EPPC List of Non-native Invasive Plants in Georgia, 2019). There has been a strong need for the development of new infertile cultivars in *L. camara* to protect the environment and the native species and provide new introductions for the nursery and landscape industries.

The new *Lantana* cultivar 'UF-1013-1' is a product of a planned breeding program at the University of Florida's Gulf Coast Research and Education Center (UF/GCREC) in Balm, Fla. The primary objective of the breeding program is to develop new infertile *Lantana* cultivars with desirable plant stature, dense branching habits, and attractive flower colors.

The new *Lantana* cultivar 'UF-1013-1' resulted from a planned cross between a proprietary breeding line DROP-25 (female parent) and cultivar 'Landmark Flame Improved' (male parent; 'Balandimfla', U.S. Plant patent application Ser. No. 11/015,489, now abandoned). The stated cross was made in fall 2010 in Balm, Fla. The new *Lantana* cultivar was discovered and selected in Balm, Fla. in April 2012 as one flowering plant within the progeny of the stated cross.

Asexual propagation of the new *Lantana* cultivar by vegetative cuttings in a controlled environment in Balm, Fla. since 2012 has shown that the unique features of this new *Lantana* cultivar are stable and reproduce true to type plants in successive generations.

Plant Breeder's Rights for this cultivar have not been applied for. The new *Lantana* cultivar 'UF-1013-1' has not been made publicly available more than one year prior to the filing of this application.

SUMMARY OF THE INVENTION

The new *Lantana* cultivar has not been observed under all possible environmental conditions. The phenotype of the new cultivar may vary with variations in environment and cultural practices such as temperature, light intensity, shading, tipping, pruning, fertilization, irrigation, and application of plant growth regulators without any change in genotype.

The following traits have been repeatedly observed and are determined to be the unique characteristics of the new *Lantana* cultivar. These characteristics in combination distinguish 'UF-1013-1' as a new and distinct cultivar of *Lantana camara:*

1. moderate plant vigor;
2. mounding and partially upwardly and spreading growth habit;
3. very dense branching;
4. compact plant form and canopy;
5. free flowering;
6. yellow- and red-colored flowers;
7. production of full, attractive plants in containers;
8. little fruiting and no or few berries, little seed production, and high level of female infertility;
9. aborted pollen and very low pollen stainability;
10. no to little hybridization potential with *Lantana depressa;*
11. approximately 4.82 picograms of nuclear DNA content in triploid somatic cells and tissues; and
12. carrying two alleles (152 and 160 base pairs (bp)) at the *Lantana*11 simple sequence repeat (SSR) marker locus, three alleles (135, 143 and 147 bp) at the *Lantana*12 SSR marker locus, and one allele (93 bp) at the *Lantana*20 SSR marker locus.

Plants of the new *Lantana camara* cultivar 'UF-1013-1' differ from plants of the female parent, DROP-25, in the following characteristics:

1. plants of the new cultivar 'UF-1013-1' are triploids, while plants of DROP-25 are tetraploids;
2. plants of the new cultivar 'UF-1013-1' are mounding and have dense branches, while plants of DROP-25 have few branches and an erratic branching habit;
3. plants of the new cultivar 'UF-1013-1' are more vigorous and taller than plants of DROP-25;
4. plants of the new cultivar 'UF-1013-1' produce no or few fruit, no or few seeds, and are highly female-infertile, while plants of DROP-25 are more female-fertile and produce more fruit;
5. plants of the new cultivar 'UF-1013-1' have very low pollen stainability or viability, while plants of DROP-25 have higher pollen stainability or viability; and
6. plants of the new cultivar 'UF-1013-1' carry two alleles (152 and 160 bp) at the *Lantana*11 marker locus, three alleles (135, 143 and 147 bp) at the *Lantana*12 marker locus and one allele (93 bp) at the *Lantana*20 marker locus, while plants of DROP-25 carry three alleles (150, 152 and 160 bp) at the *Lantana*11 marker locus, four alleles (135, 143, 145 and 147 bp) at the *Lantana*12 marker locus, and two alleles (93 and 109 bp) at the *Lantana*20 marker locus.

Plants of the new cultivar 'UF-1013-1' differ from plants of the male parent, 'Landmark Flame Improved', in the following characteristics:

1. plants of the new cultivar 'UF-1013-1' are triploids, while plants of 'Landmark Flame Improved' are diploids;
2. plants of the new cultivar 'UF-1013-1' are mounding and have a round form and canopy, while plants of 'Landmark Flame Improved' are much larger, spreading, and have an open canopy;
3. flowers of the new cultivar 'UF-1013-1' are yellow-colored when initially open and turn red when matured, while flowers of 'Landmark Flame Improved' are gold to orange;
4. plants of the new cultivar 'UF-1013-1' produce no or few fruit or seeds and are highly female-infertile, while plants of 'Landmark Flame Improved' are female-fertile and produce more fruit and seeds; and
5. Plants of the new cultivar 'UF-1013-1' have low pollen stainability or viability, while plants of 'Landmark Flame Improved' have higher pollen stainability or viability.

Plants of the new *Lantana camara* cultivar 'UF-1013-1' differ from plants of its sibling cultivar, 'UF-1013A-2A' (Bloomify™ Red), US Plant Pat. No. 29,292), in the following characteristics:

1. plants of the new cultivar 'UF-1013-1' are more compact than plants of 'UF-1013A-2A';
2. plants of the new cultivar 'UF-1013-1' have a more spreading canopy than plants of 'UF-1013A-2A';
3. flowers of the new cultivar 'UF-1013-1' are larger than plants of 'UF-1013A-2A';
4. flowers of the new cultivar 'UF-1013-1' have a darker red color than plants of 'UF-1013A-2A';
5. plants of the new cultivars 'UF-1013-1' have a higher nuclear DNA content than plants of 'UF-1013A-2A' (4.8 pg/2C vs. 4.5 pg/2C in 'UF-1013A-2A');
6. plants of the new cultivar 'UF-1013-1' carry two alleles (135 and 147 bp) at the *Lantana*12 marker locus, while plants of 'UF-1013A-2A' miss these two alleles.

Plants of the new *Lantana* cultivar 'UF-1013-1' can also be compared to the cultivar 'Landscape Bandana Red Improved' (commercial cultivar, not patented). In side-by-side comparisons conducted in Balm, Fla., plants of the new *Lantana* cultivar differed from plants of 'Landscape Bandana Red Improved' in the following characteristics:

1. plants of the new cultivar 'UF-1013-1' are shorter and narrower and more compact, while plants of 'Landscape Bandana Red Improved' are taller and wider;
2. plants of the new cultivar 'UF-1013-1' form a compact, upright canopy in containers, while plants of 'Landscape Bandana Red Improved' have drooping branches and form a very open canopy;
3. inflorescences of the new cultivar 'UF-1013-1' are larger than plants of 'Landscape Bandana Red Improved'; and
4. mature flowers of the new cultivar 'UF-1013-1' are much redder, while the mature flowers of 'Landscape Bandana Red Improved' are light pink to salmon.

Plants of the new *Lantana* cultivar 'UF-1013-1' can be compared to 'Luscious® Citrus Blend' ('Balandusbi', U.S. Plant Pat. No. 32,018). In side-by-side comparisons conducted in Balm, Fla., plants of the new *Lantana* cultivar differed from plants of 'Luscious® Citrus Blend' in the following characteristics:

1. Plants of the new cultivar 'UF-1013-1' are narrower and more compact, while plants of 'Luscious® Citrus Blend' are wider;
2. Plants of the new cultivar 'UF-1013-1' are more upright, while plants of 'Luscious® Citrus Blend' are more spreading and open;
3. Mature flowers of the new cultivar 'UF-1013-1' are red in color, while mature flowers of 'Luscious® Citrus Blend' are gold and orange in color; and
4. Plants of the new cultivar 'UF-1013-1' are highly sterile and produce little fruit, while plants of 'Luscious® Citrus Blend' produce much more fruit and have much higher levels of fertility.

DESCRIPTION OF THE FIGURES

The accompanying photographs (as shown in FIGS. 1-7) illustrate the overall appearance of the new *Lantana camara* cultivar 'UF-1013-1'. These photographs show the colors as true as can be reasonably obtained in colored reproductions of this type. Colors in the photographs may differ slightly from the color values cited in the detailed botanical description, which accurately describe the colors of the new *Lantana* cultivar.

DETAILED BOTANICAL DESCRIPTION OF THE CULTIVAR

Figure 1:
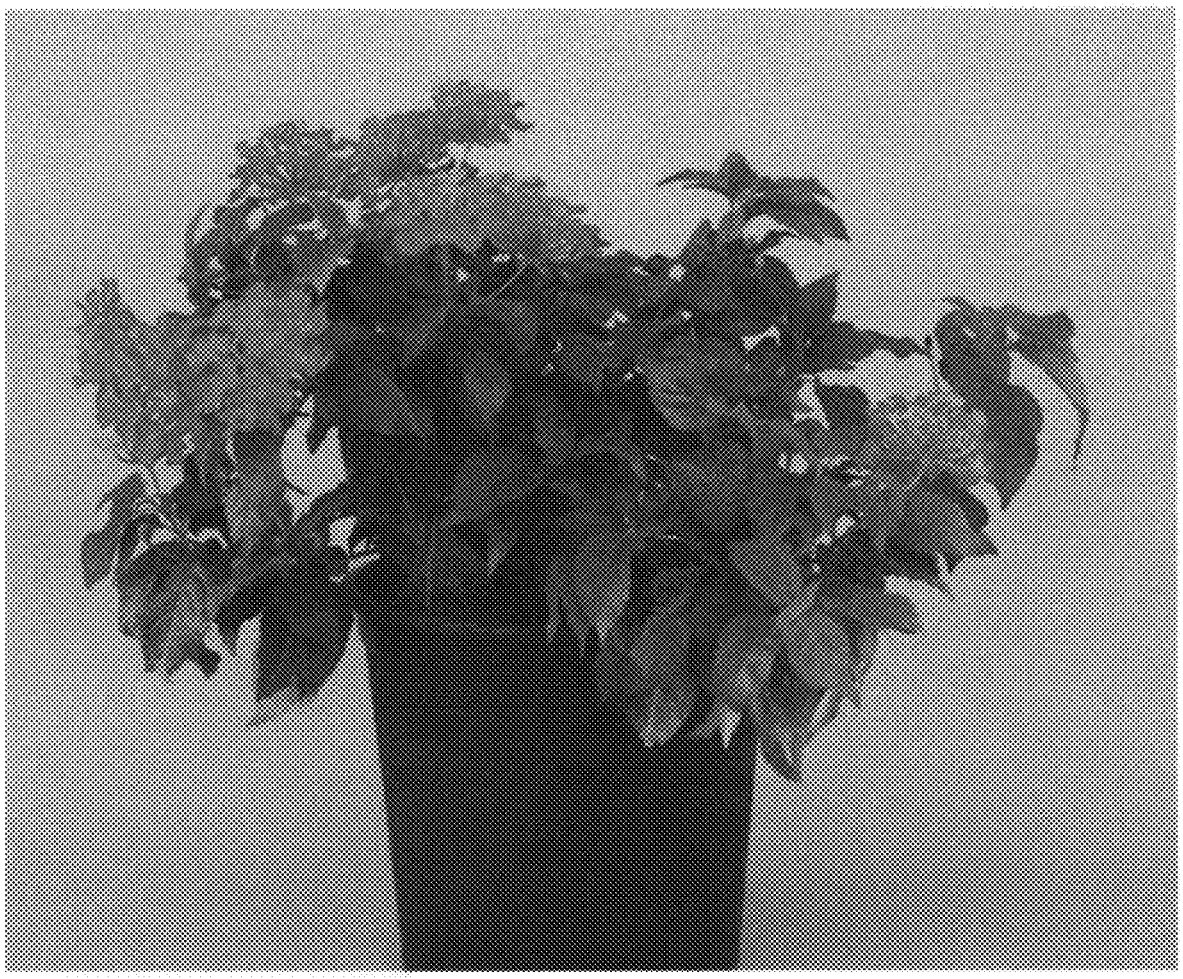
FIG. 1 shows a side perspective view of a typical flowering plant of the new *Lantana* cultivar 'UF-1013-1' to show its growth and branching habit, plant form, and flower color. The plant was grown in a gallon (16.5 cm in diameter and 16 cm tall) container and is shown at approximately 16 weeks old. The plant was propagated from cuttings and pinched once.
Figure 2:
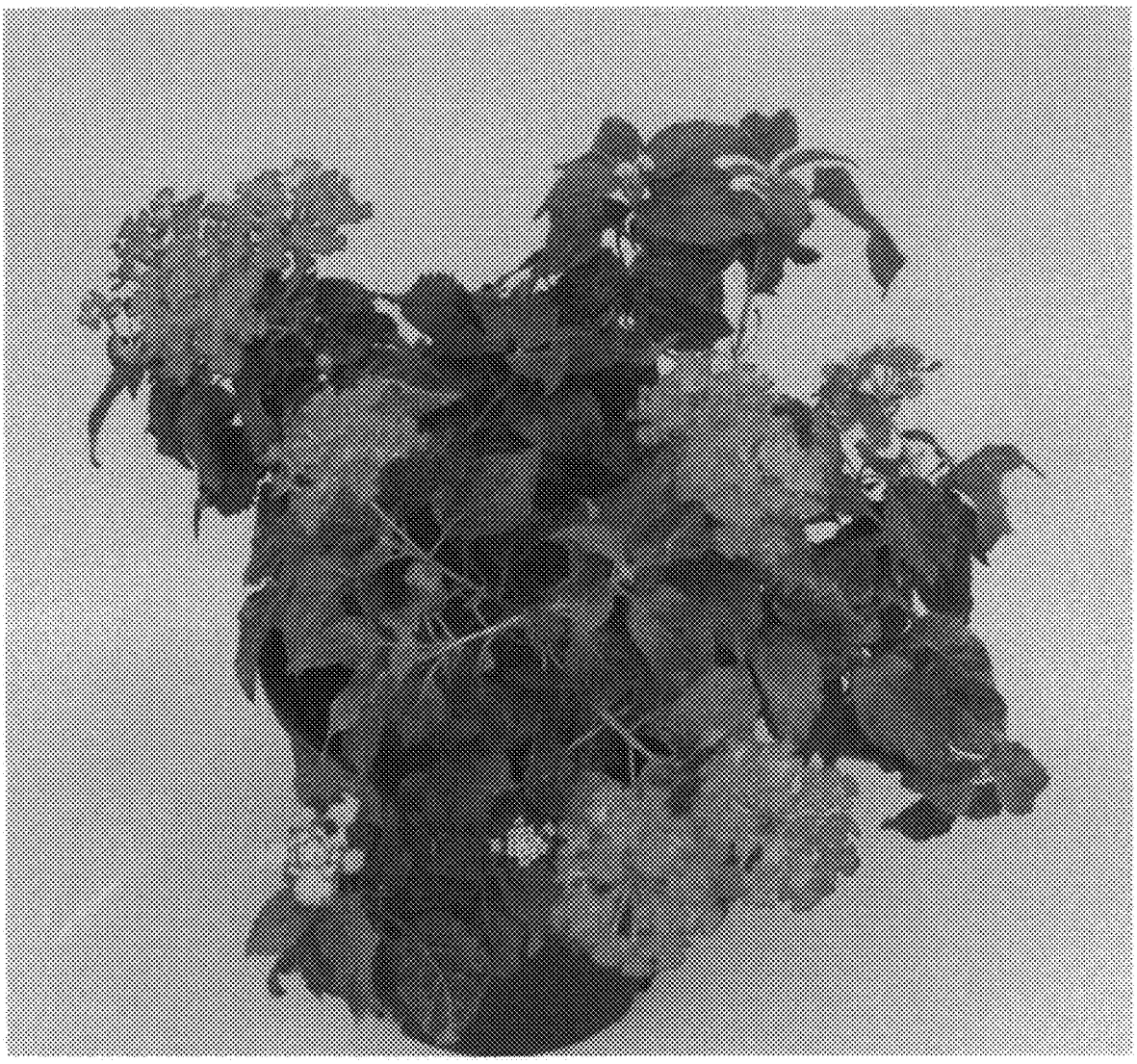
FIG. 2 shows a top view of a typical flowering plant of the new *Lantana* cultivar 'UF-1013-1' to show its growth and branching habit, plant form, and flower color. The plant was grown in a gallon (16.5 cm in diameter and 16 cm tall) container and is shown at approximately 16 weeks old. The plant was propagated from cuttings and pinched once.
Figure 3:
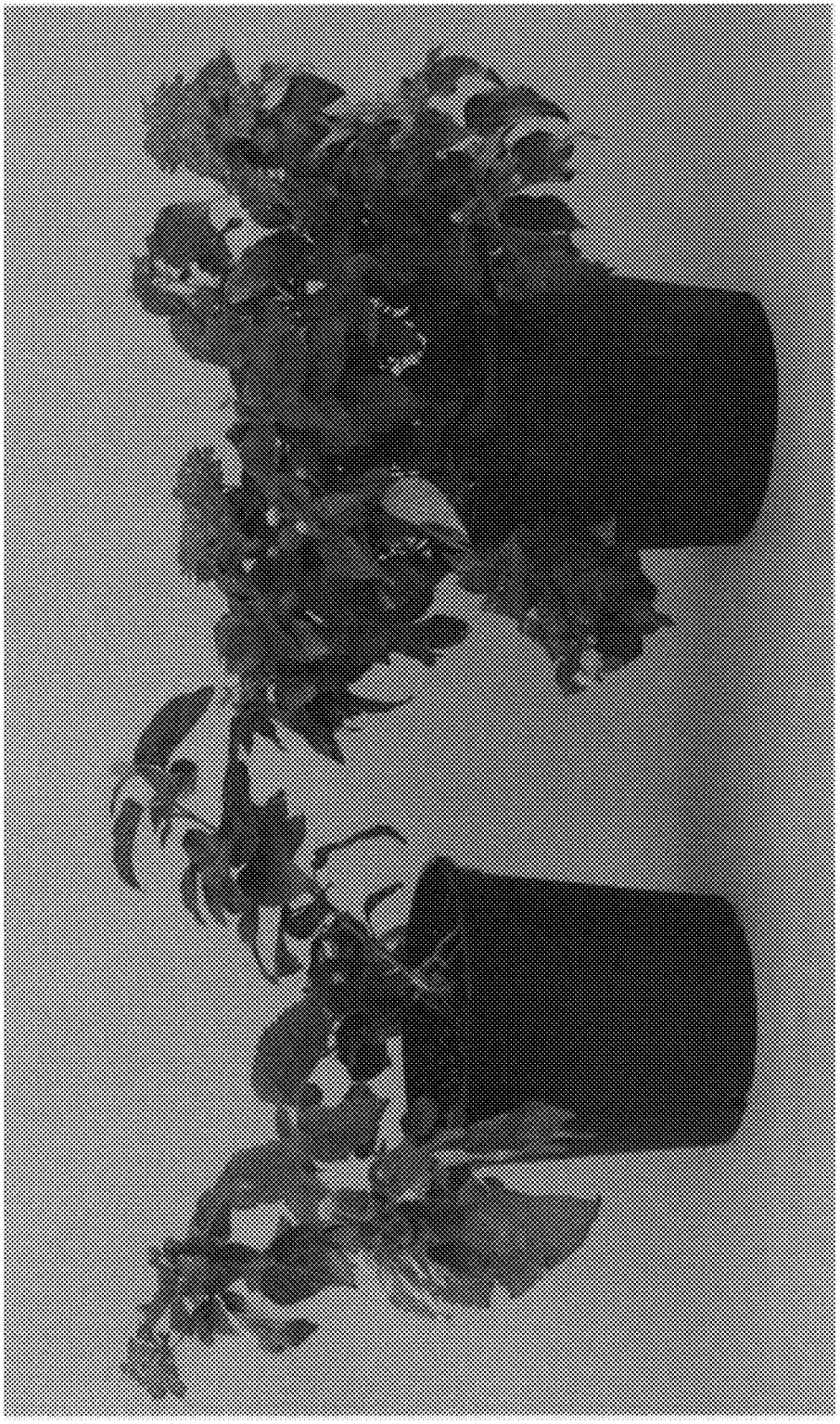
FIG. 3 shows a side perspective view of breeding line DROP-25 (left) (female parent) and the new *Lantana* cultivar 'UF-1013-1' (right) when they were grown in gallon (16.5-cm diameter) containers. They were approximately 16 weeks old grown from rooted cuttings that were pinched once.
Figure 4:
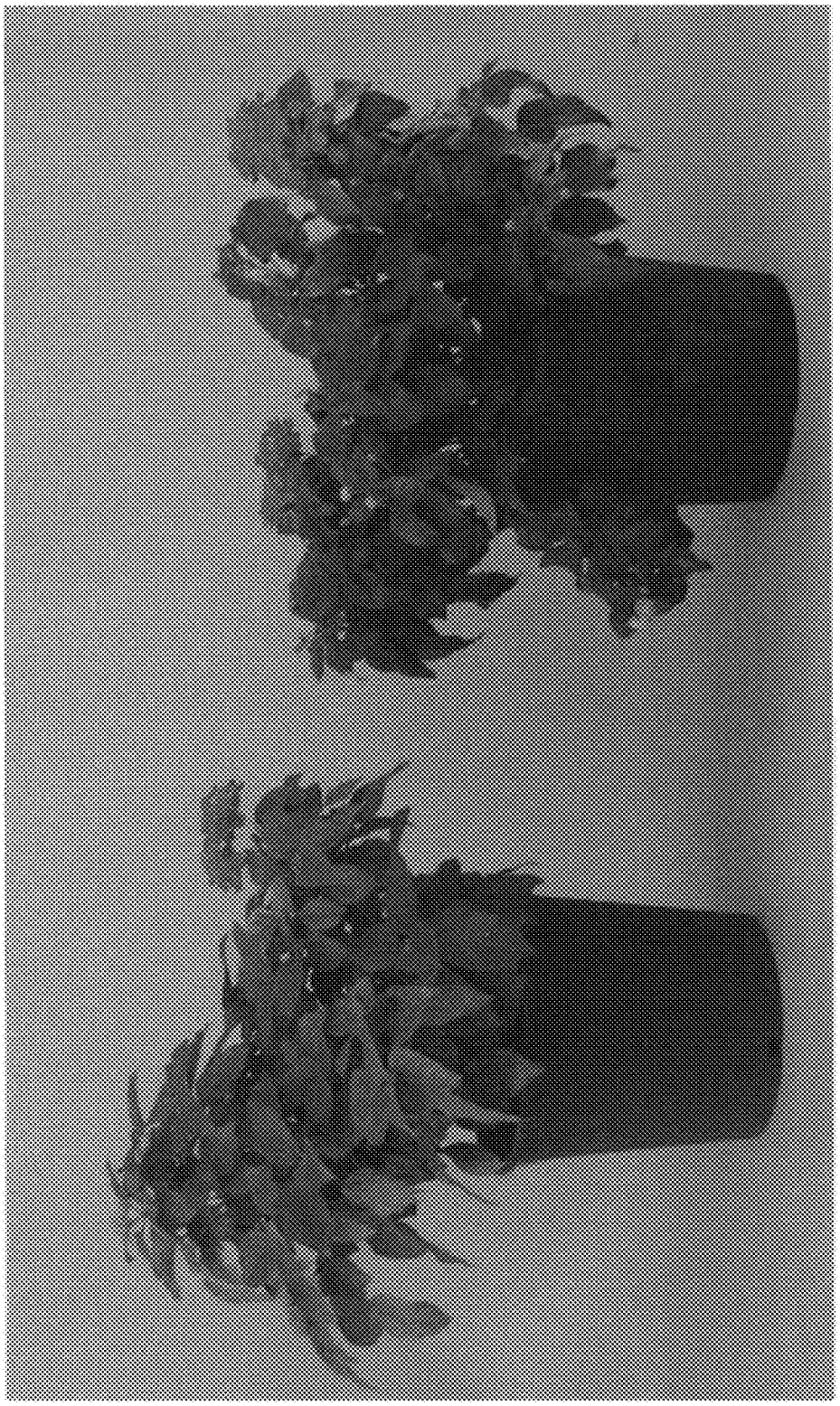
FIG. 4 shows a side perspective view of cultivar 'UF-1013A-2A' (left) and the new cultivar 'UF-1013-1' (right) when they were grown in gallon (16.5-cm diameter) containers. They were approximately 16 weeks old and grown from rooted cuttings that were pinched once.
Figure 5:
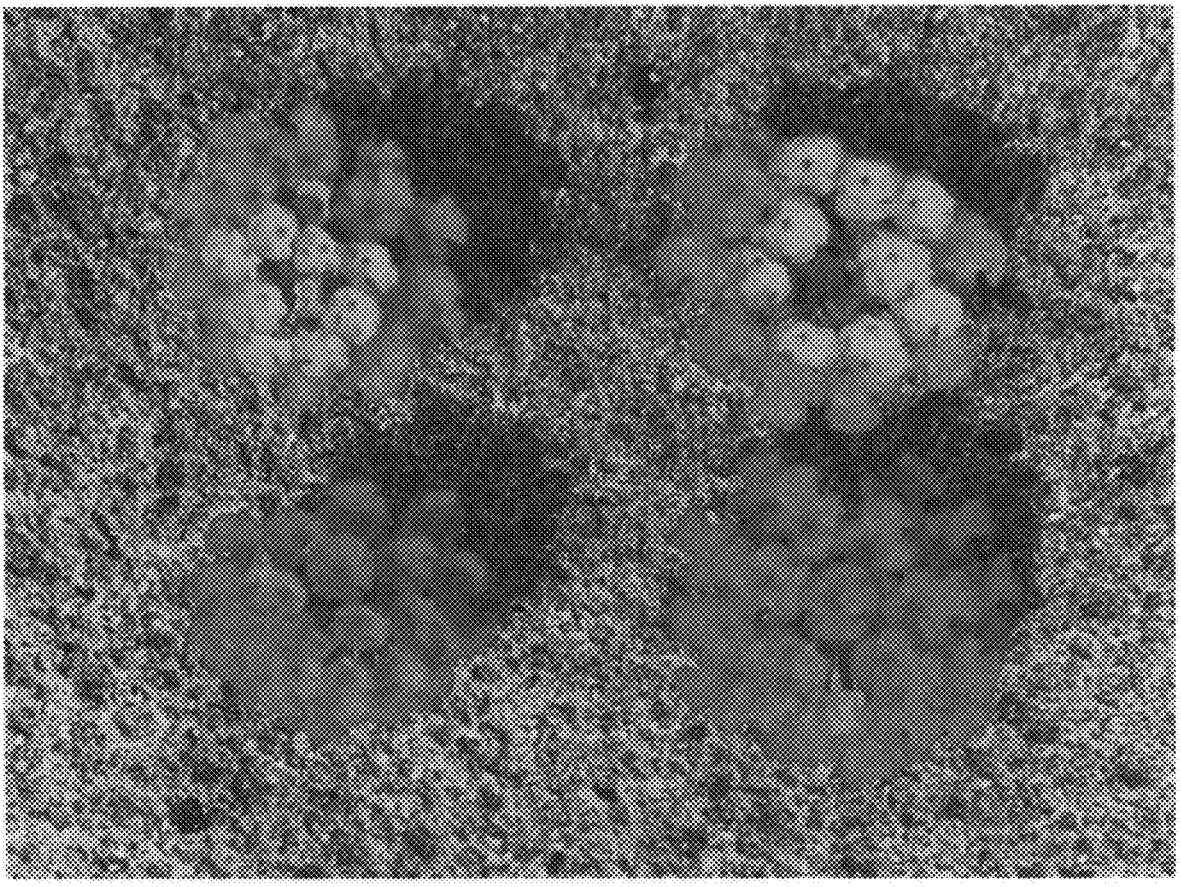
FIG. 5 shows a top view of fully open flowers of cultivar 'UF-1013A-2A' (left) and the new cultivar 'UF-1013-1' (right). The flowers were taken from plants of these cultivars grown in the ground bed in full sun in Citra, Fla.
Figure 6:
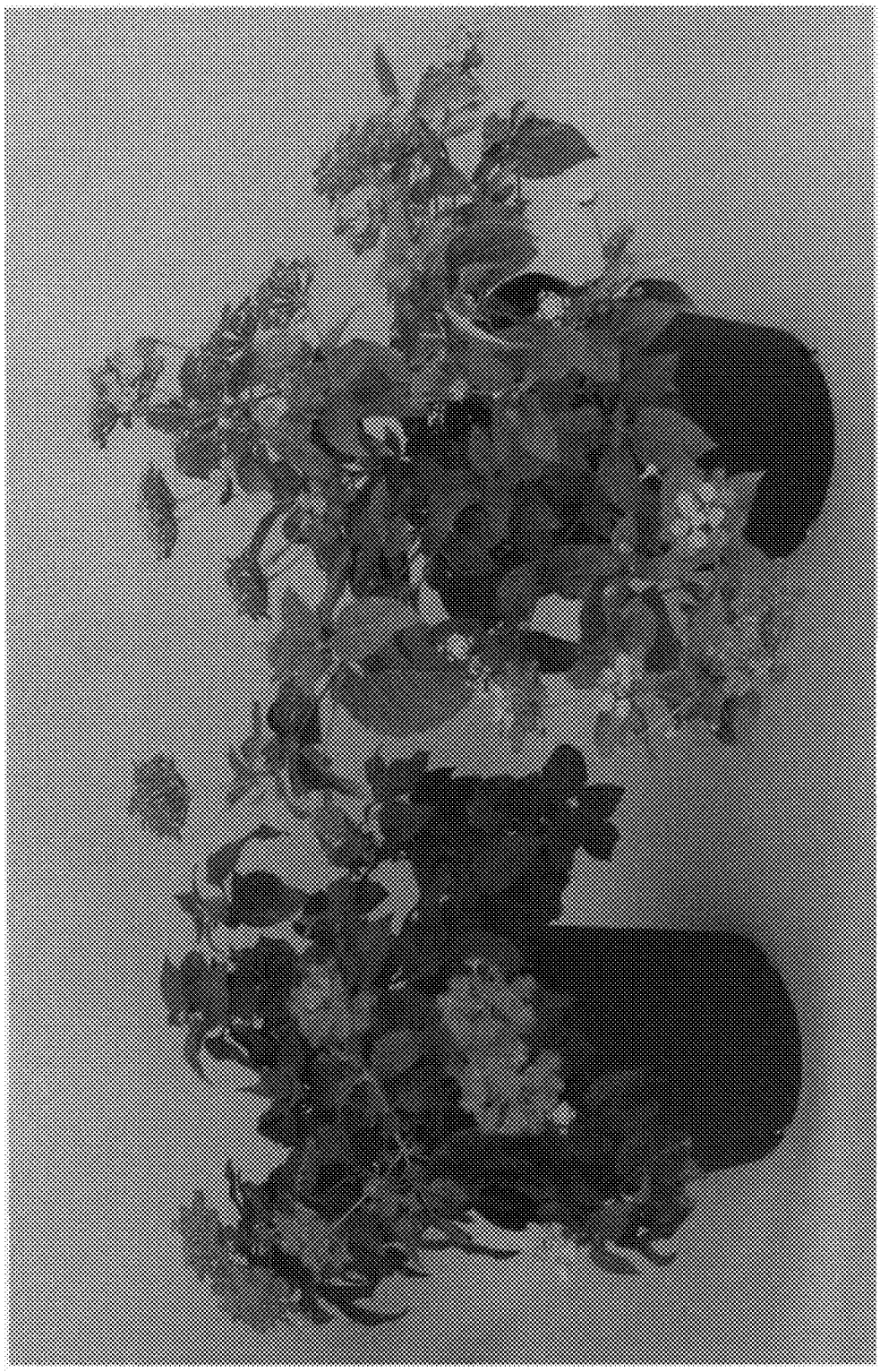
FIG. 6 shows a side perspective view of the new cultivar 'UF-1013-1' (left) and 'Landscape Bandana Red Improved' (commercial cultivar, not patented) (right) when they were grown in gallon (16.5-cm diameter) containers. They were approximately 16 weeks old and grown from rooted cuttings that were pinched once.
Figure 7:
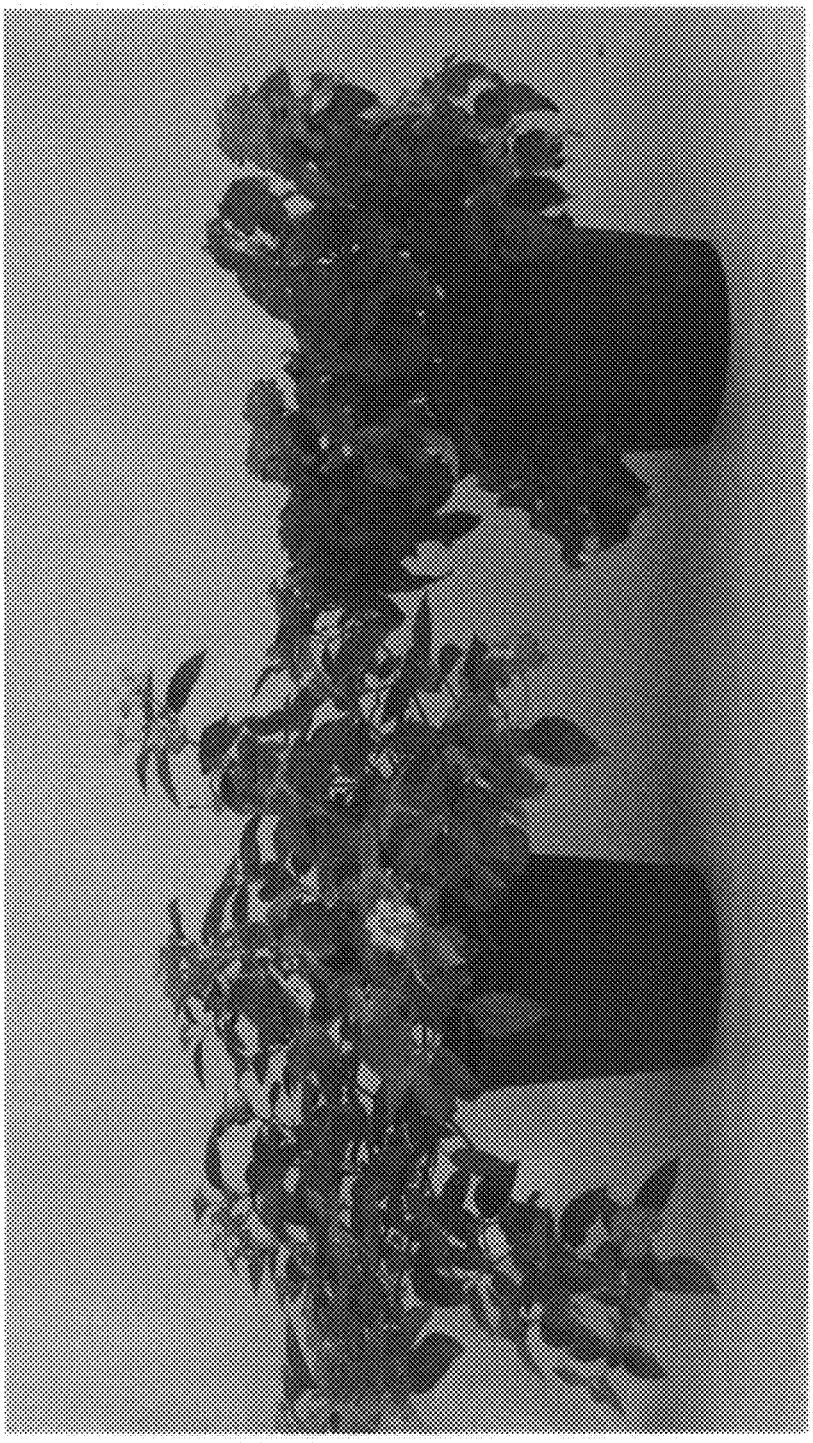
FIG. 7 shows a side perspective view of 'Luscious® Citrus Blend' (left) and the new cultivar 'UF-1013-1' (right) when they were grown in gallon (16.5-cm diameter) containers. They were approximately 16 weeks old and grown from rooted cuttings that were pinched once.

In the following description, color references are made to The Royal Horticultural Society (R.H.S.) Colour Chart, 1986 Edition, except where general terms of ordinary dictionary significance are used.

Description of Growing Conditions

Plants used for the description were grown in the fall and winter of 2019 and early spring of 2020 in Balm, Fla. for 24 weeks from when terminal cuttings were made. Cuttings were dipped into a commercial rooting hormone solution (Dip & Grow®, Dip'N Grow, Inc., Clackamas, Oreg.) on 30 Aug. 2019; rooted cuttings were potted up in gallon containers on 26 Sep. 2019. Plants in gallon containers were pinched on 10 Oct. 2019. Plants were grown in the greenhouse until 24 Feb. 2020. Plant data was taken and plant, foliage, and flower descriptions were made. During the production of the plants in the greenhouse, temperatures ranged from about 22.2° C. to about 35.5° C.

Botanical Description

Botanical classification:

*Family.*—Verbenaceae.

*Botanical name.*—*Lantana camara* (*L. camara*).

*Common name.*—*Lantana.*

*Cultivar.*—'UF-1013-1'.

Parentage:

*Female or seed parent.*—DROP-25.

*Male or pollen parent.*—'Landmark Flame Improved'.

Propagation:

*Type.*—Terminal cutting.

*Time to initiate roots.*—About nine days at 27° C.

*Time to produce rooted cuttings.*—About 25 days at 27° C.

Root description:

*Type.*—Fine, fibrous; initially glaucous white in color.

*Color.*—Close to white (RHS 155B).

*Rooting habit.*—Freely branching.

Plant description:

*Plant form.*—Flowering subshrub.

*Growth habit.*—Outwardly spreading and partially upright plant habit; mounded plant form and canopy; dense branching; two lateral branches potentially forming at every node; pinching enhances lateral branch development.

*Plant height.*—About 25 cm.

*Plant diameter.*—About 39 cm×about 34 cm.

*Lateral branches.*—Length: About 13 cm. Diameter: About 1.6 mm. Internode length: About 1.6 cm. Strength: Strong, but flexible. Texture: Rough, pubescent. Color, young: Close to yellow-green (RHS 144B). Color, woody: Closed to greyed-brown (RHS 199A/B).

*Stem.*—Quantity of main branches per plant: About four to five. Quantity of leaves per branch: About 12-13. Length of stem: About 10-13 cm. Diameter: About 0.8-2.2 mm. Length of internodes: About 1.0-2.4 cm. Texture: Pilose, and a few glandular hairs on upper surface. Color: Close to yellow green (RHS 144A and 144B).

Foliage description:

*Arrangement.*—Opposite; simple.

*Length.*—About 5.2-8.4 cm.

*Width.*—About 3.1-6.2 cm.

*Shape.*—Ovate. Apex: Acute. Base: Obtuse with truncate tendencies.

*Margin.*—Crenate to serrate.

*Teeth along margins of leaf.*—Mostly 34 to 44.

*Texture, upper and lower surfaces.*—Leathery, coarse, pubescent.

*Luster.*—Upper surface: Slightly glossy with tiny hairs. Lower surface: Dull.

*Color, developing and fully expanded foliage.*—Upper surface, developing: Close to green (RHS 147A). Upper surface, expanded: Close to green (RHS 147A). Lower surface, developing: Close to green (RHS 147B). Lower surface, expanded: Close to green (RHS 147B).

*Venation pattern.*—Arcuate.

*Color of veins.*—Upper surface: Close to green (RHS 146A). Blends in with leaf color. Lower surface: Close to green (RHS 146B/C).

*Petiole.*—Length: About 1.1-2.7 cm. Diameter: About 0.9-1.6 mm. Texture, both surfaces: Slightly pubescent. Color: Upper surface: Close to yellow-green (RHS 146C). Lower surface: Close to yellow-green (RHS 146D).

Inflorescence description:

*Flower type.*—Umbel-like, flattened semi-sphere; flowers are sessile on ovate receptacle.

*Flowering habit.*—Freely flowering, with potentially two inflorescences per node; typically about 22-30 flowers per umbel; flowering is continuous and consistent, spring until front in the autumn; flowers are self-cleaning.

*Flowering longevity on the plant.*—About one week.

*Fragrance.*—None detected.

*Inflorescence diameter.*—About 4.5 cm.

*Inflorescence height.*—About 2.4 cm.

*Number of flowers per inflorescence.*—About 22-30.

*Quantity of inflorescences per plant.*—About 15; more during the warm season.

*Flowers (fully open).*—Flower form and appearance: Flared trumpet, corolla fused, four-parted; flowers roughly rectangular in shape. Flower horizontal diameter: About 1.3 cm×about 1.1 cm. Flower length: About 2.1 cm.

*Flower buds (before showing color).*—Length: About 5.5 mm. Diameter (width): About 1.3 mm. Shape: Corolla tubes are roughly spherical to ovoid; Flower buds are nearly rectangular when viewed from the top. Color: Close to yellow-green (RHS 144D).

*Bract.*—Length: About 5.5 mm. Diameter: About 1.1 mm. Color: Close to yellow-green (RHS 144B) near base and close to green (RHS 143A) near tip. Texture: Outer surface: Hirsute. Inner surface: Glandular hairs on inner surface.

*Corolla.*—Arrangement/appearance: Single whorl of four petals fused into a flared trumpet. Tube length: About 1.4 cm. Throat and tube texture: Outer surface: Pubescent/slightly hirsute basally. Inner surface: Papillose. Tube color (mature): Outer surface: Close to greyed red (RHS 179C). Inner surface, throat: Close to greyed red (RHS 179D).

*Petal.*—Length from throat: Upper and lower petals: About 6.3 mm. Lateral petals: About 2.7 mm. Width: Upper and lower petals: About 7.7 mm. Lateral petals: About 4.4 mm. Shape: Spatulate to somewhat orbicular. Apex: Rounded. Margin: Entire. Degree of lobation: Moderate. Petal lobe texture, upper and lower surfaces: Smooth, velvety. Color: Petal lobes, when opening (immature): Upper surface: Close to yellow (RHS 13A). Toward the apex: Close to yellow (RHS 13C). Lower surface: Close to yellow (RHS 9B/C). Petal lobes, fully opened (mature): Upper surface: Close to orange red (RHS 34A). Toward the apex: Close to orange red (RHS 34B). Lower surface: Close to orange red (RHS 31C). Throat: Close to yellow (RHS 9A). Tube: Close to orange (RHS 28D).

*Calyx.*—Number of sepals: 4 sepals fused to form calyx. Length: About 2.5 mm. Width: About 1.7 mm. Shape: Lanceolate. Apex: Acute. Base: Truncate. Texture: Lower surface (inside): Pubescent. Color: Upper surface: Close to yellow-green (RHS 144A). Lower surface: Close to yellow-green (RHS 144A).

*Peduncles.*—Length: About 1.9 cm. Diameter: About 1 mm. Angle: About 12 degrees from the stem. Strength: Flexible, but strong. Texture: Pubescent. Color: Close to yellow-green (RHS 144A).

*Pedicels.*—Not observed, flowers not stalked.

*Stamens.*—Quantity/arrangement: Four per flower, joined to a floral tube. Length of filament: About 1.2 mm. Color of filament: Close to yellow (RHS 13B).

*Anther.*—Shape: Oblong. Length: About 1.2 mm. Color: Poorly developed.

*Pistils.*—Quantity: One per flower. Length: About 4.4 mm. Stigma shape: Rounded. Stigma color: Close to yellow-green (RHS 144C). Style color: Close to yellow-green (RHS 150D).

*Ovary color.*—Close to yellow-green (RHS 144A).

*Pollen.*—Amount: Most pollen grains are aborted. Approximately 98% of the observed pollen grains are not viable, and viable pollen grains are rarely observed. Color: Not able to document.

*Fruit.*—None or rarely observed.

Assessment of Female Fertility

Table 1 shows fruit production of the new *Lantana* cultivar 'UF-1013-1' and two checks ('UF-1013A-2A' and 'Pink Caprice' (commercial cultivar, not patented)) in two replicated field trials in Florida.

The two field trials were conducted at the University of Florida (UF)'s Gulf Coast Research and Education Center (GCREC) in Balm, Fla, (southwest Florida, USDA hardiness zone 9a, and AHS heat zone 10) and at UF's Indian River Research and Education Center (IRREC) in Ft. Pierce, Fla. (southeast Florida, USDA hardiness zone 9b, and AHS heat zone 9-10). The experimental design used in the Balm trial was a randomized complete block with three blocks and two plants per plot. Ground beds at the GCREC were raised about 20 cm, fumigated with Pic-Clor 60™ (Trical, Inc., Hollister, Calif.; active ingredients 1,3-dichloropropene and chloropicrin) at 448 kg per hectare in February 2015, and covered with white-on-black plastic. The experimental design used in the Ft. Pierce trial was a randomized complete block with four blocks and single-plant plots. Ground beds at the IRREC were not fumigated but treated with a pre-emergent herbicide (Sandea®, 75.0% ai (halosulfuron-methyl), Gowan Company, L.L.C., Yuma, Ariz.) at a rate of 0.1056 grams $L^{-1}$ and a 2% solution of glyphosate (Roundup WeatherMAX®, 48.8% ai, Monsanto Technology LLC, Saint Louis, Mo.) and covered with black ground cover. Plants in the two trials were grown in full sun.

At each site, 'Pink Caprice' and 'UF-1013A-2A' were included as controls. 'Pink Caprice' is very prolific in fruit (and seed) production (Czarnecki et al., 2012), while 'UF-1013A-2A' is highly infertile (Deng et al., 2017). In addition, 21 commercial cultivars with various levels of male and female fertility were randomly placed in each block at both sites.

Fruit production data were collected from each plant in the Balm and Ft. Pierce trials. The four data collections in Balm were made on 17 Aug., 14 Sep., 16 Oct., and 18 Nov., 2015, respectively. The four data collections in Ft. Pierce were made on 12 Aug., 10 Sep., 14 Oct., and 11 Nov. 2015, respectively. In each collection, 20 peduncles were randomly sampled from each plant; thus, approximately 120 peduncles were sampled for each cultivar grown in Balm, and 80 peduncles were sampled for each cultivar grown in Ft. Pierce. Fruit on all harvested peduncles were counted, regardless of maturity. An analysis of variance and separation of mean fruit production values was conducted using JMP® Pro 13.2.0 (SAS Institute Inc., Cary, N.C.) to compare the fruit production of the new *Lantana* cultivar 'UF-1013-1' with that of 'UF-1013A-2A' and 'Pink Caprice'. Mean values with the same letter within columns in Table 1 are not significantly different by the Tukey's HSD procedure at $P<0.05$.

As shown in Table 1 and reported previously (Deng et al., 2017), 'Pink Caprice' produced the largest number of fruit (drupes) among all the cultivars in the two replicated trials. Each peduncle had an average of 7.941 drupes in Ft. Pierce and 10.313 drupes in Balm, averaged to 9.127 drupes per peduncle across the two sites and four harvests. The number of drupes per peduncle for the sterile cultivar 'UF-1013A-2A' ranged from 0 to 0.050 and averaged to 0.015 across the two sites over the 4 months. The number of drupes the new *Lantana* cultivar 'UF-1013-1' produced per peduncle ranged from 0 to 0.038 and averaged to 0.009 across two experimental sites and over 4 months. This level of fruit production in the new cultivar 'UF-1013-1' represented greater than 99% reduction from the fruit production of 'Pink Caprice'.

Seed germination: Seeds were extracted from mature drupes collected from the above experiments. Seeds were cleaned, air-dried, and germinated. A subsample of seeds of 'Pink Caprice' were sent to Mid-West Seed Services in Brookings, S.D., a commercial seed testing laboratory, for seed viability tests. The new *Lantana* cultivar 'UF-1013-1' and 'UF-1013A-2A' produced few or no seeds at either site and were therefore not tested for viability. Seeds of 'Pink Caprice' showed an average of 65.0% viability, germinated readily, with an average germination percentage of 45.0% in 60 days. For 'UF-1013A-2A', no mature drupes were collected from Balm or Ft. Pierce. For the new *Lantana* cultivar 'UF-1013-1', three mature drupes were collected from the Ft. Pierce trial over four months. Three seeds were extracted, but all were abnormal when visually examined. Thus, there were no seeds from the new *Lantana* cultivar 'UF-1013-1' and 'UF-1013A-2A' for seed viability or germination tests.

Female Fertility Index (FFI): Fruit (seed) production per peduncle and seed germination are the primary factors determining *Lantana*'s female fertility. Female fertility index (FFI) was calculated by multiplying fruit production per peduncle and seed germination. The FFI for 'Pink Caprice' was 4.107. Because of the lack of seed germination data, it was not possible to calculate the FFI for the new *Lantana* cultivar 'UF-1013-1'. However, based on its triploidy and extremely low fruit production, it was expected that the FFI for the new *Lantana* cultivar 'UF-1013-1' would be close to zero.

TABLE 1

| Expt. Site | Cultivars | Fruit per peduncle 8 to 21 weeks post transplanting (WPT) | | | |
|---|---|---|---|---|---|
| | | 8 Aug. 12 | 12 Sep. 9 | 16 Oct. 7 | 21 Nov. 11 |
| Balm | New cultivar ('UF-1013-1') | 0.008 b | 0.008 b | 0 b | 0 b |
| | 'UF-1013A- 2A' (Bloomify ™ Red; U.S. Plant Pat. No. 29,292) | 0.012 b | 0.050 b | 0.025 b | 0 b |
| | 'Pink Caprice' | 14.258 a | 8.850 a | 10.117a | 8.025 a |
| | | 8 Aug. 12 | 12 Sept. 10 | 17 Oct. 14 | 21 Nov. 11 |
| Ft. Pierce | New cultivar ('UF-1013-1') | 0.013 b | 0b | 0.038 b | 0 b |
| | 'UF-1013A- 2A' (Bloomify ™ Red; U.S. Plant Pat. No. 29,292) | 0 b | 0 b | 0 b | 0 b |
| | 'Pink Caprice' | 11.588 a | 8.325 a | 6.263 a | 5.588 a |

| Expt. Site | Cultivars | Total peduncles examined (no.) | Total fruit collected (no.) | Total mature fruit collected (no.) | Average fruit per peduncle |
|---|---|---|---|---|---|
| Balm | New cultivar ('UF-1013-1') | 480 | 2 | 0 | 0.004 b |
| | 'UF-1013A- 2A' (Bloomify ™ Red; U.S. Plant Pat. No. 29,292) | 481 | 11 | 0 | 0.023 b |
| | 'Pink Caprice' | 480 | 4,950 | 1,416 | 10.313 a |
| Ft. Pierce | New cultivar ('UF-1013-1') | 320 | 4 | 3 | 0.013 b |

TABLE 1-continued

| | | | | |
|---|---|---|---|---|
| 'UF-1013A- 2A' (Bloomify ™ Red; U.S. Plant Pat. No. 29,292) | 320 | 0 | 0 | 0 b |
| 'Pink Caprice' | 320 | 2,541 | 1,832 | 7.941 a |

Assessment of Pollen Stainability

Table 2 shows pollen stainability of the new *Lantana* cultivar 'UF-1013-1' and two checks ('UF-1013A-2A' (Bloomify™ Red) and 'Pink Caprice') when their plants were grown in Balm and Ft. Pierce, Fla. in full sun in 2015. Two pollen staining experiments were conducted. In Experiment 1, newly opened flowers were collected from plants grown in Balm, Fla. in late July 2015, and anthers were extracted from the flowers and collected into 1.5-mL Eppendorf tubes. The collected anthers were stained with $10^{-6}$ M fluorescein diacetate (FDA) (Sigma-Aldrich, St. Louis, Mo.) in 0.22 M sucrose at room temperature in the dark for 1 hour (Czarnecki et al., 2014). Stained anthers were transferred onto a microscope slide and covered with a coverslip. Pollen grains in the anthers were released by gently tapping and pressing the coverslip and then examined under a fluorescent microscope. Plump, round pollen grains fluorescing bright yellowish green light were considered stainable, while misshaped, non-fluorescing, or unevenly, lightly fluorescing pollen grains were counted as non-stainable. In Experiment 2, flowers were collected from *Lantana* plants grown in Ft. Pierce, Fla. in mid-August 2015. Anther staining and pollen examination were performed as described in Experiment 1. The number of pollen grains examined for each *Lantana* cultivar in each staining experiment was between 1,094 and 2,122. Pollen stainability data (in percentage) were arcsine-transformed before analysis of variance was performed. Means with the same letter within the column of Table 2 are not significantly different by the LSD procedure at $P<0.05$. The analysis of variance and mean separation were conducted using the software JMP® Pro 13.2.0.

As shown in Table 2, the average pollen stainability of the new *Lantana* cultivar 'UF-1013-1' was 2.2%, comparable to the average pollen stainability of sterile cultivar 'UF-1013A-2A'. The average pollen stainability of 'Pink Caprice' was 73.1%. The pollen stainability (or male fertility) of the new *Lantana* cultivar 'UF-1013-1' was reduced substantially (95%) from that of 'Pink Caprice'.

TABLE 2

| | Pollen grains examined (no.) | | Pollen stainability (%) | | |
|---|---|---|---|---|---|
| Cultivar | Experiment 1 | Experiment 2 | Experiment 1 | Experiment 2 | Average |
| 'UF-1013-1' | 1464 | 1840 | 2.0 b | 2.4 b | 2.2 b |
| 'UF-1013A-2A' (Bloomify ™ Red; U.S.Plant Pat. No. 29,292) | 2122 | 1466 | 1.5 b | 4.5 b | 3.0 b |
| 'Pink Caprice' | 1271 | 1094 | 70.8 a | 75.3 a | 73.1 a |

Assessment of Hybridization Potential With *Lantana depressa*

Table 3 shows the hybridization potential of the new *Lantana* cultivar 'UF-1013-1' with *L. depressa* as compared to 'UF-1013A-2A' and 'Pink Caprice'.

Hand pollination experiments were performed in a greenhouse at GCREC in Balm, Fla. in June and July 2015 to assess the hybridization potential of the new *Lantana* cultivar 'UF-1013-1', as a male or female parent, with *L. depressa*. 'UF-1013A-2A' and 'Pink Caprice' were included in the pollination experiments as an infertile and a fertile check, respectively. Stock plants of all *Lantana* cultivars and *L. depressa* were grown in 1-gallon plastic containers and arranged into three blocks and in each block, they were randomly placed on the benches. The experimental unit consisted of two containerized plants. Air temperature inside the greenhouse was from 21° C. to 33° C. No supplemental lighting was provided. Plants were drip-irrigated twice per day. Fresh anthers were collected from mature unopened flowers of male parents and applied immediately to emasculated flowers of female parents. At maturity, fruit produced by the pollinated flowers were collected and counted, and seeds were extracted and sown to determine seedling emergence.

Fruit set data (in percentage) were arcsine-transformed before analysis of variance was performed in JMP® Pro 13.2.0. Mean values with the same letter within the column are not significantly different by the LSD procedure at $P<0.05$.

As shown in Table 3, 'Pink Caprice', as a male parent, caused an average of 8.6% fruit set on *L. depressa*. When pollinated with *L. depressa*, 'Pink Caprice' flowers showed 19.9% fruit set. Seeds from crosses between 'Pink Caprice' and *L. depressa* or vice versa showed 11.1% or 15.8% seedling emergence. As a male parent, 'UF-1013A-2A' did not cause any fruit set on *L. depressa* flowers, nor did it set any fruit after hand-pollination with *L. depressa*. A total of 389 *L. depressa* flowers were pollinated with the new cultivar, and none of the pollinated flowers set fruit, resulting in 0% fruit set (Table 3). When the new cultivar was used as the female parent, it did not set any fruit after it was hand-pollinated with *L. depressa*. Thus, the new cultivar did not hybridize with *L. depressa* (Table 3). These data confirm the high level of male and female infertility in the new cultivar.

TABLE 3

| | *L. depressa* as the female parent | | | *L. depressa* as the male parent | | | |
|---|---|---|---|---|---|---|---|
| Cultivar | Flowers pollinated (no.) | Fruit set (%) | Seedling emergence (%) | Flowers pollinated (no.) | Fruit set (%) | Seedling emergence (%) | |
| 'UF-1013-1' | 389 | 0 b | — | 496 | 0 b | — | |
| 'UF-1013A-2A' (Bloomify ™ Red; U.S. Plant Pat.. No. 29,292) | 353 | 0 b | — | 558 | 0 b | — | Deng et al. (2017) |
| 'Pink Caprice' | 388 | 8.6 a | 11.1 | 452 | 19.9 a | 15.8 | Deng et al. (2017) |

Assessment of Nuclear DNA Contents

As shown in Table 4, the new cultivar 'UF-1013-1' has an average nuclear DNA content of 4.82 pg/2C and is a triploid. The nuclear DNA content was determined using a CyFlow® Cube 6 flow cytometer (Sysmex Partec GmbH, Münster, Germany) and the procedure described by Doležel et al. (Estimation of Nuclear DNA Content in Plants Using Flow Cytometry, Nat. Protoc. 2:2233-2244 (2007)) and modified by Cao et al. (2014). Pea cultivar 'Ctirad' (*Pisum sativum*) with a nuclear content of 9.09 pg/2C was used as the internal reference for this determination in this study. The new cultivar 'UF-1013-1' has 6.2% higher nuclear DNA content than 'UF-1013A-2A' does (4.82 pg/2C vs. 4.54 pg/2C). The ploidy level of 'UF-1013-1' was determined by comparing its nuclear DNA content with the DNA content of known diploid, triploid and tetraploid *Lantana* cultivars.

TABLE 4

| Cultivars | Mean nuclear DNA content (pg/2C) | Standard deviation (SD) | Ploidy level |
|---|---|---|---|
| 'UF-1013-1' | 4.82 | 0.11 | 3× |
| 'UF-1013A-2A' (Bloomify ™ Red; U.S.Plant Pat. No. 29,292) | 4.54 | 0.08 | 3× |
| 'Pink Caprice' | 6.25 | 0.17 | 4× |

DNA Fingerprints

As shown in Table 5, the new cultivar 'UF-1013-1' carries two alleles (152 and 160 base pairs (bp)) at the *Lantana*11 SSR marker locus, three alleles (135, 143 and 147 bp) at the *Lantana*12 SSR marker locus, and one allele (93 bp) at the *Lantana*20 SSR marker locus.

This DNA fingerprint analysis was performed using three pairs of *Lantana*-specific SSR primers. *Lantana* genomic DNA was isolated from *Lantana* leaves in Balm, Fla. Primers were developed as described by Gong and Deng (Development and Characterization of Microsatellite Markers for Caladiums (*Caladium* Vent.), Plant Breeding 130(5) (2011)) from SSR-enriched *Lantana* genomic sequences (Gong and Deng, unpublished). Nucleotide sequences of the three pairs of primers are: *Lantana*11F: (M13 tail sequence)-TGCAATTGGAGGCTTTTTCT, and *Lantana*11R: AAAGCAGCTTCAAGTTTGTGC; *Lantana*12F: (M13 tail sequence)-GGATGAGATGATAAGGTAGGGTGT, and *Lantana*12R: TTGGTGGTGATGACTTTGATTC. *Lantana*20F: (M13 tail sequence)-AGAATCAGGGTTTGGGGTTG, and *Lantana*20R: TCGTAGCCACCACTCCTCAC. The M13 tail sequence was 5'-CCCAGTCACGACGTTG-3'. Polymerase chain reaction (PCR) amplification, capillary electrophoresis, and allele scoring were performed at the United State Department of Agriculture/Agricultural Research Services Fruit and Tree Nut Research Laboratory, Byron, Ga., using a procedure previously described by Chen et al. (Genome-wide Characterization and Selection of Expressed Sequence Tag Simple Sequence Repeat Primers for Optimized Marker Distribution and Reliability in Peach, Tree Genet. Genome 10:1271-1279 (2014)) with minor modifications.

As shown in Table 5, the female parent of the new cultivar, breeding line DROP-25, carries three alleles (150, 152 and 160 bp) at the *Lantana*11 marker locus, four alleles (135, 143, 145 and 147 bp) at the *Lantana*12 marker locus, and two alleles (93 and 109 bp) at the *Lantana*20 marker locus.

TABLE 5

| Lantana cultivars | Alleles amplified by SSR markers (size of alleles in base pairs) | | | | | |
|---|---|---|---|---|---|---|
| | Marker Lantana11 | | | | Marker Lantana12 | |
| | 150 | 152 | 156 | 160 | 135 | 143 |
| New cultivar ('UF-1013-1') | | + | | + | + | + |
| 'UF-1013A-2A' (Bloomify ™ Red; U.S. Plant Pat. No. 29,292) | + | + | | + | | + |
| DROP-25 | + | + | | + | + | + |
| 'Pink Caprice' | | + | + | + | | + |

| Lantana cultivars | Alleles amplified by SSR markers (size of alleles in base pairs) | | | | | |
|---|---|---|---|---|---|---|
| | Marker Lantana12 | | | | Lantana20 | |
| | 145 | 147 | 150 | 152 | 93 | 109 |
| New cultivar ('UF-1013-1') | | + | | | + | |
| 'UF-1013A-2A' (Bloomify ™ Red; U.S. Plant Pat. No. 29,292) | + | | | | + | |
| DROP-25 | + | + | | | + | + |
| 'Pink Caprice' | + | | + | + | + | + |

"+" indicates the presence of the respective alleles in the cultivars.

I claim:

1. A new and distinct *Lantana camara* plant named 'UF-1013-1', as illustrated and described herein.

* * * * *